United States Patent
Kergosien

(10) Patent No.: US 10,828,247 B2
(45) Date of Patent: Nov. 10, 2020

(54) MAKE UP KIT COMPRISING A BASE COMPOSITION RESISTANT TO MAKE UP REMOVAL

(71) Applicant: L'OREAL, Paris (FR)

(72) Inventor: Guillaume Kergosien, Chaville (FR)

(73) Assignee: L'OREAL, Paris (FR)

( * ) Notice: Subject to any disclaimer, the term of this patent is extended or adjusted under 35 U.S.C. 154(b) by 54 days.

(21) Appl. No.: 14/648,177

(22) PCT Filed: Dec. 4, 2013

(86) PCT No.: PCT/EP2013/075535
§ 371 (c)(1),
(2) Date: May 28, 2015

(87) PCT Pub. No.: WO2014/086861
PCT Pub. Date: Jun. 12, 2014

(65) Prior Publication Data
US 2015/0297499 A1     Oct. 22, 2015

Related U.S. Application Data

(60) Provisional application No. 61/754,040, filed on Jan. 18, 2013.

(30) Foreign Application Priority Data

Dec. 5, 2012 (FR) .................... 12 61691

(51) Int. Cl.
| | | |
|---|---|---|
| *A61K 8/891* | (2006.01) | |
| *A61K 8/31* | (2006.01) | |
| *A61K 8/34* | (2006.01) | |
| *A61Q 3/02* | (2006.01) | |
| *A61Q 3/04* | (2006.01) | |
| *A61K 8/81* | (2006.01) | |
| *A61K 8/84* | (2006.01) | |
| *A61K 8/87* | (2006.01) | |
| *A61K 8/88* | (2006.01) | |
| *A61K 8/89* | (2006.01) | |

(52) U.S. Cl.
CPC ............... *A61K 8/891* (2013.01); *A61K 8/31* (2013.01); *A61K 8/34* (2013.01); *A61K 8/8105* (2013.01); *A61K 8/84* (2013.01); *A61K 8/87* (2013.01); *A61K 8/88* (2013.01); *A61K 8/89* (2013.01); *A61Q 3/02* (2013.01); *A61Q 3/04* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 2002/0192168 A1* | 12/2002 | Blin | ...... | A61K 8/4973 424/61 |
| 2004/0166075 A1* | 8/2004 | Jeanne-Rose | ............ | A61K 8/19 424/70.1 |
| 2010/0012548 A1* | 1/2010 | McClanahan | .......... | A45D 29/20 206/581 |

FOREIGN PATENT DOCUMENTS

| | | | |
|---|---|---|---|
| DE | 200 18 601 U1 | 3/2001 | |
| FR | 2939678 A1 * | 6/2010 | ............... A61K 8/37 |
| WO | WO-02/26199 A2 | 4/2002 | |

OTHER PUBLICATIONS

Versamid 930 <https://www.ulprospector.com/en/na/Inks/Detail/1767/221875/VERSAMID-930>. Available Apr. 15, 2008; accessed Sep. 8, 2016.*
Eastman. Eastotac H-142W Technical Data Sheet <https://productcatalog.eastman.com/tds/ProdDatasheet.aspx?product=71016204&pn=Eastotac+H-142W+Resin#-ga=2.82741973.258074251.1579548619-1733565993.1579548619> available Dec. 1, 2005; accessed Jan. 20, 2020 (Year: 2005).*
English translation of FR-2939678-A1 (Year: 2010).*

* cited by examiner

*Primary Examiner* — Nicole P Babson
(74) *Attorney, Agent, or Firm* — Polsinelli PC

(57) ABSTRACT

The present invention relates to a kit for make-up and/or care of nails and/or false nails, comprising: —a composition C1 for make-up and/or care of nails and/or false nails comprising at least one film-forming polymer, said polymer being insoluble in acetone, methyl acetate, and ethyl acetate, and —a make-up removal composition C2 comprising at least one volatile solvent S2 selected from the group consisting of $C_2$-$C_5$ alcohols, $C_5$-$C_{12}$ alkanes, and mixtures thereof, said solvent S2 being able to solubilize the film-forming polymer of composition C1.

13 Claims, No Drawings

MAKE UP KIT COMPRISING A BASE COMPOSITION RESISTANT TO MAKE UP REMOVAL

CROSS REFERENCE TO RELATED APPLICATIONS

This application is a National Phase filing under 35 U.S.C. § 371 of PCT/EP2013/075535 filed on Dec. 4, 2013; and this application claims priority to Application No. 1261691 filed in France on Dec. 5, 2012, and this application claim the benefit of U.S. Provisional Application No. 61/754,040 filed on Jan. 18, 2013. The entire contents of each application are hereby incorporated by reference.

The present invention relates to a kit for make-up and/or care of nails and/or false nails, as well as to a method for make-up and/or care of nails and/or false nails.

Conventionally, make-up or care of nails or false nails is achieved by means of liquid make-up or care compositions further called nail varnishes. This nail varnish is generally applied in the form of layers superposed to the surface of the nail (or of the false nail) to be made up or cared for, while observing an intermediate drying step between each applied varnish layer.

In order to notably avoid that the pigments of the nail varnish compositions leave spots on the nails (or false nails) or make them yellow, the prior application of a transparent base composition, or «base-coat», is recommended. However this make-up and care method does not prove to be entirely satisfactory.

Conventional base-coat compositions are soluble in the solvents of conventional make-up removers. Therefore, when it is desired to change the varnish color, it is necessary to remove the make-up from the whole of the nail varnish layer and of the base-coat layer, and to then apply again a new layer of base-coat on the nail (or the false nail) before a new make-up or care of the nails (or the false nails). This represents a waste of time and causes excessive consumption of the base-coat composition.

Further, successive make-up removals with conventional make-up removers such as acetone or ethyl acetate tend to make the nails fragile.

Therefore, there exists a need for a novel method for make-up and/or care of nails and/or false nails with which it is possible to get rid of the drawbacks of the make-up methods described above.

The present invention aims at proposing a method for make-up and/or care of nails and/or false nails allowing the nails or false nails to be rapidly made up again.

The present invention aims at proposing a method for make-up and/or care of nails and/or false nails with which it is possible to reduce the contact of solvents with the nails.

The present invention also aims at proposing a method for make-up and/or care of nails with which it is possible to avoid fragility of the nails caused by repeated make-up removals.

More specifically, the present invention aims at providing a kit comprising a base composition which cannot be removed with conventional make-up removers, but which is removable with a specific make-up remover on the one hand, and a specific make-up remover for removing said base composition on the other hand.

The present invention relates to a kit for make-up and/or care of nails and/or false nails, comprising:
 a composition C1 for make-up and/or care of nails and/or false nails comprising at least one film-forming polymer, said polymer being insoluble in acetone, methyl acetate and ethyl acetate, and
 a composition C2 for make-up removal comprising at least one volatile solvent S2 selected from the group formed by $C_2$-$C_5$ alcohols, $C_5$-$C_{12}$ alkanes, and mixtures thereof, said solvent S2 being able to solubilize the film-forming polymer of composition C1.

The film-forming polymer of composition C1 is insoluble in acetone.

According to an embodiment, the latter is also insoluble in liquid ketones at room temperature such as methylethylketone, methylisobutylketone, diisobutylketone, isophorone and cyclohexanone.

The film-forming polymer of the composition C1 is insoluble in methyl acetate and ethyl acetate.

According to an embodiment, the latter is also insoluble in $C_3$-$C_4$ alkyl acetate, such as propyl acetate, n-propyl acetate, isopropyl acetate, n-butyl acetate, isobutyl-acetate and tert-butyl acetate.

Preferably the film-forming polymer of composition C1 is insoluble in ethyl acetate.

The solvents of the invention are organic or mineral solvents, which are physiologically acceptable.

By «volatile solvent», is meant in the sense of the invention a solvent which may evaporate in contact with keratinic materials in less than one hour, at room temperature and at atmospheric pressure. The volatile solvent(s) of the invention are liquid solvents at room temperature, having non-zero vapor pressure, at room temperature and at atmospheric pressure, in particular ranging from 0.13 Pa to 40,000 Pa ($10^{-3}$ to 300 mm of Hg), in particular ranging from 1.3 Pa to 13,000 Pa (0.01 to 100 mm of Hg), and more particularly ranging from 1.3 Pa to 1300 Pa (0.01 to 10 mm of Hg).

By «non-volatile solvent», is meant a solvent remaining on the nails at room temperature and at atmospheric pressure for at least several hours and notably having a vapor pressure of less than $10^{-3}$ mm of Hg (0.13 Pa).

By «solvent able to solubilize the film-forming polymer of composition C1», it is meant that a solvent is able to remove make-up from a nail or a false nail coated with a dry layer of composition C1.

Generally, a solvent is «able to solubilize» a polymer when a mixture of said solvent and of said polymer forms a homogeneous solution, and not a dispersion or biphasic mixture.

The volatile solvent S2 of the composition C2 is selected from the group consisting of $C_2$-$C_5$ alcohols, $C_5$-$C_{12}$ alkanes and mixtures thereof.

By «$C_2$-$C_5$ alcohol», is meant an organic compound comprising at least one hydroxyl group —OH, preferably exactly one hydroxyl group —OH, and with 2 to 5 carbon atoms and which is moreover liquid at room temperature, i.e. from 15° C. to 30° C.

The $C_2$-$C_5$ alcohols suitable for the invention notably include ethanol and isopropanol.

By «$C_5$-$C_{12}$ alkane», is meant a cyclic or acyclic, linear or branched, saturated hydrocarbon compound, exclusively consisting of carbon atoms and hydrogen atoms, which is moreover liquid at room temperature, i.e. from 15° C. to 30° C.

Within the scope of the present invention, alkanes preferably comprise from 5 to 12, preferentially from 5 to 10, advantageously from 5 to 8 carbon atoms.

The $C_5$-$C_{12}$ alkanes suitable for the invention notably include heptane and isomers thereof, decane and isomers thereof, cyclohexane and dodecane and isomers thereof.

The make-up removal composition C2 is different from the make-up composition C1.

The compositions C1 and C2 are contained, within the kit of the invention, in distinct containers.

Typically, the make-up removal composition C2 essentially consists of volatile solvents.

Typically, the make-up removal composition C2 comprises at least 80%, preferably at least 90%, preferentially at least 95%, advantageously at least 99% by weight of volatile solvents, such as the solvent S2.

The composition C2 essentially consists of the volatile solvent S2. The composition C2 may further comprise a moisturizing agent and/or a perfuming agent, such as an essential oil for example.

Preferably, the composition C2 exclusively consists of the volatile solvent S2.

In the composition C1 of the kit according to the invention, the film-forming polymer is generally in solution in at least one volatile solvent S1 selected from the group consisting of $C_2$-$C_5$ alcohols, $C_5$-$C_{12}$ alkanes and mixtures thereof.

The solvent S1 is therefore able to solubilize the film-forming polymer of composition C1.

The solvent S1 of the composition C1 is preferably identical with the solvent S2 of the composition C2.

As a solvent S1 suitable for the invention, mention may be made of ethanol and isopropanol, decane, heptane, dodecane, cyclohexane and isomers thereof, and mixtures thereof.

Typically, the composition C1 comprises from 10 to 95% by weight, preferably from 30 to 80% by weight, better from 50 to 80% by weight, or even from 60 to 80% by weight of solvent S1, based on the total weight of said composition.

The film-forming polymer of the composition C1 is preferably selected from the group consisting of polyamides, polyureas, polyurethanes, silicone resins and aliphatic and cycloaliphatic hydrocarbon polymers.

The film-forming polymer of composition C1 is preferably selected from the group consisting of polyamides and aliphatic and cycloaliphatic hydrocarbon polymers.

Within the composition C1, a single film-forming polymer or a mixture of film-forming polymers may be used.

According to an embodiment, the composition C1 comprises a total content of film-forming polymer(s) greater than or equal to 5%, in particular comprised from 5 to 50% by weight, notably from 10 to 45% by weight, in particular from 20 to 45% by weight based on the total weight of said composition C1.

By «film-forming polymer» is meant a polymer capable of forming, by itself or in the presence of an auxiliary film-forming agent, an insulatable, notably continuous film on a support, notably on keratinic materials.

The film-forming polymer of the composition C1 is preferably a synthetic polymer, of the radical type or of the polycondensate type.

This may be a random polymer or a sequenced polymer, also called a «block copolymer».

Within the scope of the present invention, the term of «block copolymer» designates a copolymer consisting of blocks of different compositions, connected together in linear sequences. These copolymers may also be designated as «sequenced copolymers».

In particular, the block copolymers consist of at least two blocks, preferably of two or three blocks. These copolymers are therefore preferably selected from diblock copolymers or triblock copolymers.

They may for example be illustrated as follows: (block A) (block B) for diblock copolymers and (block A) (block B) (block A) or (block B) (block A) (block B) for triblock copolymers.

According to the invention, multiblock copolymers designate copolymers comprising more than three blocks.

The block copolymers according to the invention may also be selected from star block copolymers or radial block copolymers. These copolymers have a single branching point from which emerge several blocks. In particular, such a star copolymer having n blocks (with n≥3) bound to the branching point is called a star copolymer with n blocks (or radial copolymer).

By «polyamide», is meant a polymer containing amide groups —CO=O)—NH-stemming from the polymerization of a mixture of monomers comprising aliphatic, cycloaliphatic, or aromatic diacid compounds, including two —COOH functions on the one hand and aliphatic, cycloaliphatic or aromatic diamine compounds, including two —$NH_2$ functions.

For example, a polyamide of formula:

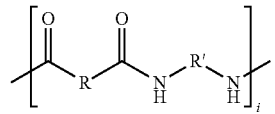

stems from the polymerization of diacids of formula HOOC—R—COOH and of diamines of formula $H_2N$—R'—$NH_2$.

According to the composition of the diacid and diamine monomers, the polyamides are classified into aliphatic, cycloaliphatic, semi-aromatic and aromatic polyamides. Depending on the type of recurrent units, the polyamides may be homopolymers or copolymers.

Preferably, the film-forming polymer is selected from polyamides of formula (I):

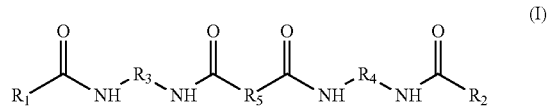

wherein:
$R_1$ and $R_2$ represent $C_1$-$C_{50}$, preferably $C_1$-$C_{20}$, hydrocarbon groups, or polyamide units,
$R_3$ and $R_4$ represent divalent $C_1$-$C_{20}$, preferably $C_1$-$C_{10}$, hydrocarbon radicals, and
$R_5$ represents a divalent $C_1$-$C_{100}$, preferably $C_{10}$-$C_{50}$, hydrocarbon radical.

In formula (I), $R_1$ and/or $R_2$ are typically linear or branched alkyl groups.

In formula (I), $R_3$, $R_4$ and/or $R_5$ are typically linear or branched alkyl groups.

In formula (I), $R_3$ and/or $R_4$ may be aliphatic, cycloaliphatic or aromatic groups.

In formula (I), $R_5$ may be an aliphatic, cycloaliphatic or aromatic group.

By «polyurea» is meant a polymer containing urea groups —NH—(C=O)—NH-stemming from the polymerization of a mixture of monomers comprising aliphatic, cycloaliphatic or aromatic diisocyanate compounds, including two —NCO functions, on the one hand, and aliphatic or aromatic diamine compounds, including two —NH$_2$ functions, on the other hand.

For example, a polyurea of formula:

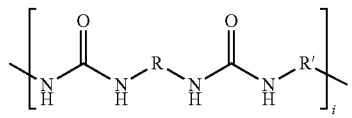

stems from the polymerization of diisocyanates of formula OCN—R—NCO and of diamines of formula H$_2$N—R'—NH$_2$.

Preferably, the film-forming polymer of the composition C1 is selected from polyureas of formula (II):

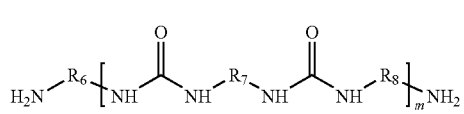

wherein:
- $R_6$ and $R_8$ represent divalent $C_1$-$C_{50}$ preferably $C_1$-$C_{20}$ hydrocarbon radical, or $Si_1$—$Si_{100}$ preferably $Si_1$—$Si_{50}$ polysiloxane units,
- $R_7$ represents a divalent aliphatic, cycloaliphatic or aromatic $C_1$-$C_{30}$, preferably $C_1$-$C_{20}$, hydrocarbon radical, and
- m is comprised between 1 and 1,000, preferably between 1 and 500.

In formula (II), $R_6$ and/or $R_8$ are typically linear or branched alkyl groups.

By «polyurethane», is meant a polymer containing urethane or carbamate —NH—(C=O)—O— groups stemming from the polymerization of a mixture of monomers comprising aliphatic, cycloaliphatic or aromatic diisocyanate compounds, including two —NCO functions, on the one hand, and aliphatic, cycloaliphatic, or aromatic diol compounds, including two —OH functions, on the other hand.

For example, a polyurethane of formula:

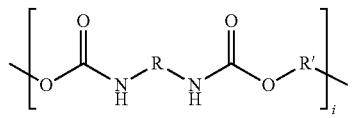

stems from the polymerization of diisocyanates of formula OCN—R—NCO and of diols of formula HO—R'—OH.

Preferably, the film-forming polymer of composition C1 is selected from polyurethanes of formula (III):

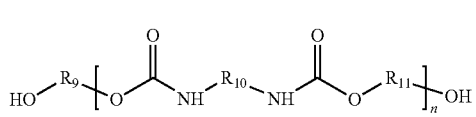

wherein:
- $R_9$ and $R_{11}$ represent divalent $C_1$-$C_{50}$, preferably $C_1$-$C_{20}$, hydrocarbon radicals, or $Si_1$—$Si_{100}$, preferably $Si_1$—$Si_{50}$, polysiloxane units,
- $R_{10}$ represents an aliphatic cycloaliphatic or aromatic divalent $C_1$-$C_{30}$, preferably $C_1$-$C_{20}$, hydrocarbon radical, and
- n is comprised between 1 and 1,000, preferably between 1 and 500.

In formula (III), $R_9$ and/or $R_{11}$ are typically linear or branched alkyl groups.

By «silicone resin», is meant a silsesquioxane polymer preferably containing units of formula (IV):

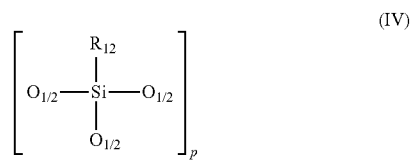

wherein:
- $R_{12}$ represents a $C_1$-$C_6$, preferably $C_1$-$C_3$, alkyl group, preferably a methyl group, and
- p is comprised between 1 and 2,000, preferably between 5 and 1,000, said polymer being such that at least 50% of the silicon atoms of said polymer are present within identical or different units of formula (IV).

Within a unit of formula (IV), each oxygen atom is bound to two silicon atoms and each silicon atom of the unit of formula (IV) is bound to three oxygen atoms and to a group $R_{12}$.

Preferably, the film-forming polymer of composition C1 is selected from silicone resins in which at least 60%, preferentially at least 70%, advantageously at least 80%, of the silicon atoms of said polymer are present within identical or different units of formula (IV).

By «hydrocarbon» compound is meant a compound comprising in majority carbon and hydrogen atoms and optionally heteroatoms such as oxygen, nitrogen or sulfur. A hydrocarbon compound preferably exclusively consists of carbon and hydrogen atoms.

By «aliphatic hydrocarbon polymers», is meant a polymer in majority stemming from the polymerization of a mixture of identical or different acyclic olefin monomers, such as $C_2$-$C_6$ alkenes, including one or two unsaturations, for example selected from ethylene, propylene, butylene, butadiene, pentene, pentadiene and isoprene.

By «cycloaliphatic hydrocarbon polymers», is meant a polymer in majority stemming from the polymerization of a mixture of identical or different cyclic olefin monomers, such as cyclopentadiene, dicyclopentadiene, and methyldicyclopentadiene, or a polymer in majority stemming from the polymerization of a mixture of aromatic hydrocarbon monomers, the polymer being then partly or totally hydrogenated.

The film-forming polymer of composition C1 is preferably an aliphatic or cycloaliphatic hydrocarbon polymer selected from aliphatic or cycloaliphatic hydrocarbon tackifying resins.

By «aliphatic or cycloaliphatic hydrocarbon tackifying resin», is meant a polymer or a copolymer of olefins or a polymer or a copolymer of partly or totally hydrogenated aromatic hydrocarbon monomers.

These may be hydrogenated indene/methylstyrene/styrene copolymers marketed under the name of «REGALITE» by Eastman Chemical, in particular REGALITE R1090, REGALITE R1100, REGALITE S1100, and REGALITE S5100, or under the name of ARKON P-90, ARKON P-100, and ARKON P-115, by Arakawa.

These may also be aliphatic pentadiene resins such as those stemming from the polymerization of a majority of 1,3-pentadiene (trans or cis piperylene) monomers and of a minority of monomers selected from isoprene, butane, 2-methyl-2-butene, pentene, 1,4-pentadiene and mixtures thereof. These resins may have a molecular weight ranging from 1,000 to 2,500 g/mol. Such resins of 1,3-pentadiene are for example marketed under the reference names of PICCOTAC 95 by Eastman Chemical, ESCOREZ 1102, ESCOREZ 1304, ESCOREZ 1310LC, ESCOREZ 1315 by Exxon Chemicals, Wingtack 95 by Cray Valley.

These may also be diene resins of cyclopentadiene dimers such as those stemming from the polymerization of dicyclopentadiene, of methyldicyclopentadiene, of other pentadiene dimers, and mixtures thereof. These resins generally have a molecular weight ranging from 500 to 800 g/mol, such as for example those marketed under the reference of ESCOREZ 5380, ESCOREZ 5300, ESCOREZ 5400, ESCOREZ 5415, ESCOREZ 5490, by Exxon Mobil Chem., and the resins SUKOREZ SU-90, SUKOREZ SU-100, SUKOREZ SU-110, SUKOREZ SU-100S, SUKOREZ SU-200, SUKOREZ SU-210, SUKOREZ SU-490, SUKOREZ SU-400, by Kolon.

These may further be hydrogenated resins stemming from the polymerization of pentadiene such as those marketed under the name of EASTOTAC H-100E, EASTOTAC H-115E, EASTOTAC C-100L, EASTOTAC C-115L, EASTOTAC H-100L, EASTOTAC H-115L, EASTOTAC C-100R, EASTOTAC C-115R, EASTOTAC H-100R, EASTOTAC H-115R, EASTOTAC C-100W, EASTOTAC C-115W, EASTOTAC H-100W, EASTOTAC H-115W, by Eastman Chemical Co.

Alternatively, this may be a mixture of aliphatic or cycloaliphatic hydrocarbon tackifying resins such as described above.

According to an alternative, the kit of the invention is such that:
the film-forming polymer of composition C1 is a polyamide, notably of formula (I) as described above, and
the volatile solvent S2 of the composition C2 is a $C_2$-$C_5$ alcohol, optionally in a mixture with a $C_5$-$C_{12}$ alkane.

According to this alternative, S2 is preferably ethanol.

Alternatively, according to this alternative, S2 is preferably a mixture of ethanol and heptane, notably a 50/50 mixture.

According to this alternative, the composition C1 preferably comprises at least one volatile solvent S1 comprising at least one $C_2$-$C_5$ alcohol, optionally in a mixture with a $C_5$-$C_{12}$ alkane.

Preferably, the volatile solvent S1 is ethanol.

According to this alternative, S1 is preferably identical with S2.

According to another alternative, the kit of the invention is such that:
the film-forming polymer of the composition C1 is selected from the group consisting of aliphatic and cycloaliphatic hydrocarbon polymers, and
the volatile solvent S2 of the composition C2 is a $C_5$-$C_{12}$ alkane, optionally in a mixture with a $C_2$-$C_5$ alcohol.

According to this alternative, S2 is preferably heptane.

According to this alternative, the composition C1 preferably comprises at least one volatile solvent S1 comprising at least one $C_5$-$C_{12}$ alkane, optionally in a mixture with a $C_2$-$C_5$ alcohol.

Preferably, the volatile solvent S1 is heptane.

According to this alternative, S1 is preferably identical with S2.

According to an embodiment, the kit of the invention further comprises:
a composition C3 of nail varnish comprising at least one film-forming polymer different from the film-forming polymer of composition C1, and preferably at least one pigment, and optionally
a make-up removal composition C4 comprising a volatile solvent selected from the group consisting of $C_2$-$C_4$ alkyl acetates and ketones.

The make-up removal composition C4 is different from the make-up removal composition C2.

Preferably, the composition C4 in majority consists of acetone or ethyl acetate.

Preferably, the composition C4 is not able to solubilize the film-forming polymer of composition C1.

Preferably, the composition C4 is free of $C_5$-$C_{12}$ alkanes and of $C_2$-$C_5$ alcohols.

The make-up removal composition C4 typically comprises at least 80%, preferably at least 90%, preferentially at least 95%, advantageously 99% by weight of volatile solvents.

The film-forming polymer of the composition C3 cannot be removed as a make-up by the composition C2 of the kit of the invention.

The film-forming polymer of the composition C3 is typically selected from derivatives of polysaccharides, such as cellulose and guar gum derivatives. A preferential derivative of polysaccharides, suitable for the invention, may be nitrocellulose or a polysaccharide ester or alkylether.

By «polysaccharide ester or alkylether», is meant a polysaccharide formed with recurrent units including at least two identical or different rings and having a substitution degree per saccharide unit comprised between 1.9 and 3 and preferably comprised between 2.2 and 2.9 and more particularly between 2.4 and 2.8. The functionalization of the hydroxyl groups into ester and/or alkylether functions and/or the functionalization of carboxylic groups into ester functions are designated by substitution.

In other words, this may be a polysaccharide, partially or totally substituted with ester and/or alkylether groups. Preferably, the hydroxyl groups may be substituted with $C_2$-$C_4$ alkylether and/or ester functions.

In particular mention may be made of cellulose esters, such as cellulose acetobutyrates or cellulose acetopropionates; cellulose alkylethers like ethylcelluloses and ethylguars.

According to a preferred particular embodiment, the film-forming polymer of the composition C3 is selected from polysaccharides and polysaccharide derivatives, preferably from among nitrocellulose and ethers and esters of notably $C_2$-$C_4$ polysaccharides, and more preferentially is selected from cellulose acetobutyrates, cellulose acetopropionates, ethylcelluloses, ethylguars and mixtures thereof.

According to a particularly preferred embodiment, the film-forming polymer is selected from cellulose derivatives such as nitrocellulose, cellulose acetobutyrate, cellulose acetopropionate and ethylcellulose.

According to an embodiment, the composition C3 comprises a total content of film-forming polymer(s) greater than or equal to 5%, in particular comprised between 1 and 30% by weight, notably between 5 and 25% by weight, in particular between 10 and 20% by weight, based on the total weight of said composition C3.

The composition C3 generally comprises at least one solvent, selected from physiologically acceptable organic and mineral solvents.

The organic solvents may in particular be selected from:
- ketones liquid at room temperature such as methylethylketone, methylisobutylketone, diisobutylketone, isophorone, cyclohexanone and acetone, and
- short chain esters (including a total of 3 to 8 carbon atoms) such as ethyl acetate, methyl acetate, propyl acetate, n-propyl acetate, isopropyl acetate, n-butyl acetate, isobutyl acetate, ter-butyl acetate, and isopentyl acetate and
- mixtures thereof.

Preferably, the solvent of the composition C3 is acetone, ethyl acetate or butyl acetate.

The solvent of the composition C3 is advantageously not able to solubilize the film-forming polymer of composition C1.

In particular, the composition C3 is preferably free of $C_5$-$C_{12}$ alkanes and of $C_2$-$C_5$ alcohols.

The total solvent content in the composition C3 may range from 5% to 95%, preferably from 30 to 80%, advantageously from 50% to 80%, or even from 60 to 80% by weight based on the total weight of said composition.

The composition C1 is preferably transparent.

As used here, the term of "transparent" means that the layer C1 has a HAZEBYK index of less than 5 as measured with a brilliance meter of the KYKHAZEGLOSS type.

The composition C3 according to the invention and optionally the composition C1 according to the invention may further comprise a coloring agent selected from the group consisting of soluble coloring agents, pigments, mothers-of-pearls and flakes.

The coloring agent(s) is(are) present in a total content of more than 0.01% by weight based on the total weight of the composition, preferably ranging from 0.1 to 5%, advantageously from 0.2 to 1% by weight based on the total weight of said composition.

By «soluble coloring agents», organic, mineral or organometal compounds should be understood, soluble in the composition C3 and intended to color said composition.

The coloring agents are for example Sudan Red, DC Red 17, DC Green 6, β-carotene, soya bean oil, Sudan brown, DC Yellow 11, DC Violet 2, DC Orange 5, and quinoline yellow.

By «pigments», should be understood particles of any shape, either white or colored, mineral or organic particles, insoluble in the composition C3 and intended to color said composition.

By «mothers-of-pearls», should be understood iridescent particles of any shape, notably produced by certain mollusks in their shell or well synthesized.

The pigments may be white or colored, mineral and/or organic. Mention may be made, from among mineral pigments, of titanium dioxide, optionally surface-treated, zirconium or cerium oxides, as well as zinc, iron oxides (black, yellow or red) or chromium oxides, manganese violet, ultramarine blue, chromium hydrate and ferric blue, metal powders such as aluminum powder, copper powder.

From among organic pigments, mention may be made of carbon black, pigments of the D & C type, and lacquers based on cochineal carmine, barium, strontium, calcium, aluminum.

Mention may also be made of pigments with an effect such as particles including a natural or synthetic, organic or mineral substrate, for example glass, acrylic resins, polyester, polyurethane, polyethylene terephthalate resins, ceramics, aluminas and either covered or not with metal substances such as aluminum, gold, copper, bronze, or metal oxides such as titanium dioxide, iron oxide, chromium oxide, mineral or organic pigments and mixtures thereof.

The mother-of-pearl pigments may be selected from white mother-of-pearl pigments such as mica covered with titanium, or bismuth oxychloride, colored mother-of-pearl pigments such as titanium mica covered with iron oxides, titanium mica covered with ferric blue and chromium oxide notably, titanium mica covered with an organic pigment of the aforementioned type as well as mother-of-pearl pigments based on bismuth oxychloride.

It is also possible to use pigments with goniochromatic properties, notably with liquid crystals or multilayer pigments.

It is also possible to use optical brighteners or fibers optionally coated with optical brighteners.

The compositions C1 and C3 of the kit according to the invention may further comprise one or several fillers, notably in a content ranging from 0.01% to 50% by weight, based on the total weight of the composition, preferably ranging from 0.01% to 30% by weight.

By «fillers», particles should be understood of any shape, colorless or white, mineral or synthetic, insoluble in the medium of the composition regardless of the temperature at which the composition is made. These fillers are notably used for modifying the flow properties or the texture of the composition.

The fillers may be mineral or organic of any shape, platelet-shaped, either spherical or oblong, regardless of the crystallographic form (for example sheet-like, cubic, hexagonal, orthorhombic, etc.). Mention may be made of talcum, mica, silica, kaolin, polyamide powders (Nylon®) (Orgasol® from Atochem), poly-β-alanine and polyethylene powders, powders of tetrafluoroethylene polymers (Teflon®), lauroyl-lysine, starch, boron nitride, polymeric hollow microspheres such as those of polyvinylidene chloride/acrylonitrile such as Expancel® (Nobel Industrie), copolymers of acrylic acid (Polytrap® from Dow Corning) and silicon resin microbeads (Tospearls® from Toshiba, for example), particles of elastomeric polyorganosiloxanes, precipitated calcium carbonate, magnesium carbonate and hydrocarbonate, hydroxyapatite, hollow silica microspheres (Silica Beads® from Maprecos), glass or ceramic microcapsules, metal soaps derived from carboxylic organic acids having from 8 to 22 carbon atoms, preferably from 12 to 18 carbon atoms, for example zinc, magnesium or lithium stearate, zinc laurate, magnesium myristate.

The compositions C1 and C3 may also further comprise adjuvants or additives, notably selected from plasticizers, coalescence agents, preservatives, waxes, thickeners, perfumes, UV filters, cosmetic actives for the care of nails, spreading agents, anti-foam agents and dispersants.

The present invention also relates to a make-up removal method for nails and/or false nails using a kit according to the invention.

The present invention thus relates to a make-up removal method for nails and/or false nails comprising the application of a make-up removal composition C2 on a nail or a false nail coated with a base coating consisting of at least one layer of composition C1, by which said base coating is removed from the nail or the false nail, said compositions C1 and C2 being as defined above.

According to an embodiment, the make-up removal method of the invention further comprises a preliminary step for make-up of the nails and/or the false nails, consisting of applying on a nail or a false nail, a make-up composition C1 as defined above, by which a base coating is deposited, consisting of at least one layer of composition C1 on a nail or a false nail.

Said base coating is intended to be removed as a make-up, a few hours or a few days after, with the make-up removal composition C2 of the kit of the invention.

Between the make-up step with which a base coating is deposited and the make-up removal step by which said base coating is removed, the user typically applies:

- a make-up and/or care by using for example the composition C3 or any other nail varnish composition, and then a few hours or a few days after,
- a make-up remover by for example using the composition C4 for removal of the make-up of the kit of the invention or any other make-up remover (provided that the latter does not remove the make-up of the base coating).

The sequence of both steps above forms a make-up/make-up removal cycle which may be repeated several times.

The user may thus carry out one, two, three, or even up to ten make-up/make-up removal cycles.

The kit of the invention thus allows the user to remove make-up and again apply make-up on a split nail, or even change the varnish color at will, rapidly and non-aggressively for the nail, which existing make-up methods cannot provide.

For example it is possible to contemplate the change in the varnish color every day of the week and to perform make-up removal of the base coating with the composition C2 at the end of the week.

Further, the kit of the invention gives the possibility of carrying out several make-up removals of the varnish layer without drying the nail, since the latter remains protected from the make-up removal agent by the base coating.

According to an embodiment, each step for applying the method described above is followed by a drying step, with which the volatile solvents are evaporated. The weight percentages given in this application may be assimilated to the dry material weight percentage of the applied compounds.

By «comprise one» or «include one» should be understood «comprise at least one» or «include at least one», except if explicitly specified otherwise.

EXAMPLES

The invention will now be illustrated by means of the following examples.

Example 1

A base coating composition according to the invention is prepared by solubilizing 40% by weight of polyamide resin (VERSAMID® 930 BASF) in 60% by weight of a 50/50 mixture of absolute ethanol and of n-heptane.

Make-Up

A base coating is deposited on the nails by applying the thereby prepared composition. After drying, a layer of conventional colored varnish composition based on nitrocellulose is deposited on the base coating.

Make-Up Removal

After drying, the colored varnish composition layer as a make-up is removed with acetone, without altering the base coating. Next, said base coating is as for it removed with a 50/50 ethanol/heptane mixture.

Example 2

A base coating composition according to the invention is prepared by solubilizing 40% by weight of hydrocarbon tackifying resin (Eastotac™ Resin H-142W—Eastman Chemical Company) in 60% by weight of n-heptane.

Make-Up

A base layer is deposited on the nails by applying the thereby prepared composition. After drying, a conventional colored varnish composition layer based on nitrocellulose is deposited on the base coating.

Make-Up Removal

After drying, the colored varnish composition layer is removed as a make-up with acetone, without altering the base coating. Next, said base coating is as for it removed with heptane.

The invention claimed is:

1. A kit for make-up and/or care of nails and/or false nails, comprising:
   a transparent composition C1 for make-up and/or care of nails and/or false nails consisting of one film-forming polymer and a volatile solvent S1 selected from the group of consisting of $C_5$-$C_{12}$ alkanes, said solvent S1 being able to solubilize the film-forming polymer of the composition C1, said film-forming polymer being insoluble in acetone, methyl acetate, and ethyl acetate, and wherein said one film-forming polymer is selected from the group of polyureas, polyurethanes, silicone resins, aliphatic hydrocarbon polymers, and cycloaliphatic hydrocarbon polymers; and
   a make-up removal composition C2 comprising at least one volatile solvent S2 selected from the group consisting of $C_2$-$C_5$ alcohols, $C_5$-$C_{12}$ alkanes, and mixtures thereof, said solvent S2 being able to solubilize the film-forming polymer of the composition C1.

2. The kit according to claim 1, wherein the solvents S1 and S2 are identical.

3. The kit according to claim 1, wherein the film-forming polymer of the transparent composition C1 is a poluyrea of formula (II):

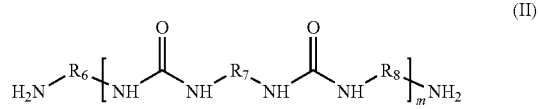

wherein:
   $R_6$ and $R_8$ represent divalent $C_1$-$C_{50}$ hydrocarbon radicals, or $Si_1$—$Si_{100}$ polysiloxane units,
   $R_7$ represents a divalent aliphatic, cycloaliphatic, or aromatic $C_1$-$C_{30}$ hydrocarbon radical, and
   m is comprised between 1 and 1,000.

4. The kit according to claim 1, wherein the film-forming polymer of the transparent composition C1 is a polyurethane of formula (III):

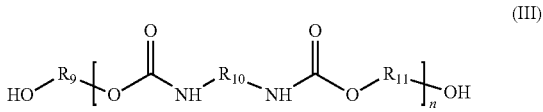

wherein:
   $R_9$ and $R_{11}$ represent divalent $C_1$-$C_{50}$ hydrocarbon radicals, or $Si_1$—$Si_{100}$ polysiloxane units,
   $R_{10}$ represents a divalent aliphatic, cycloaliphatic, or aromatic $C_1$-$C_{30}$ hydrocarbon radical and
   n is comprised between 1 and 1,000.

5. The kit according to claim 1, wherein the film-forming polymer of the transparent composition C1 is a silicone resin comprising at least one unit of formula (IV):

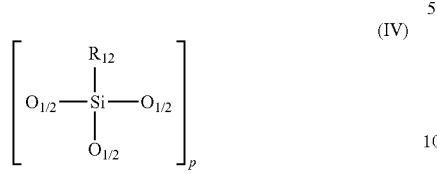

wherein:
$R_{12}$ represents a $C_1$-$C_6$ alkyl group, and
p is comprised between 1 and 2,000
said polymer being such that at least 50% of the silicon atoms of said polymer are present within units of formula (IV), either identical or different.

6. The kit according to claim 1, wherein the film-forming polymer of the transparent composition C1 is an aliphatic or cycloaliphatic hydrocarbon polymer selected from aliphatic or cycloaliphatic hydrocarbon tackifying resins.

7. The kit according to claim 1, wherein:
the volatile solvent S2 of the composition C2 is a $C_2$-$C_5$ alcohol, optionally in a mixture with a $C_5$-$C_{12}$ alkane.

8. The kit according to claim 1, wherein:
the film-forming polymer of the transparent composition C1 is selected from the group consisting of aliphatic and cycloaliphatic hydrocarbon polymers, and the volatile solvent S2 of the composition C2 is a $C_5$-$C_{12}$ alkane, optionally in a mixture with a $C_2$-$C_5$ alcohol.

9. The kit according to claim 1, further comprising:
a nail varnish composition C3 comprising at least one film-forming polymer, different from the film-forming polymer of transparent composition C1, and optionally
a make-up removal composition C4 comprising a volatile solvent selected from the group consisting of $C_2$-$C_4$ alkyl acetates and ketones.

10. The kit according to claim 6, wherein:
the volatile solvent S2 of the composition C2 is a $C_2$-$C_5$ alcohol, optionally in a mixture with a $C_5$-$C_{12}$ alkane.

11. The kit according to claim 7, wherein:
the volatile solvent S2 of the composition C2 is a $C_2$-$C_5$ alcohol, optionally in a mixture with a $C_5$-$C_{12}$ alkane.

12. A method for removing make-up from nails and/or false nails, comprising the application of a make-up removal composition C2 on a nail or a false nail coated with a base coating consisting of at least one layer of transparent composition C1, by which said base coating is removed from the nail or false nail, said compositions C1 and C2 being as defined in claim 1.

13. The method according to claim 12, comprising a preliminary step for applying on a nail or a false nail, said transparent composition C1, by which a base coating is deposited, consisting of at least one layer of said transparent composition C1 on a nail or a false nail.

* * * * *